United States Patent [19]
Claassen

[11] 3,936,491
[45] Feb. 3, 1976

[54] ADAMANTYLENE COMPOUNDS
[75] Inventor: Volkert Claassen, Weesp, Netherlands
[73] Assignee: U.S. Philips Corporation, New York, N.Y.
[22] Filed: Nov. 29, 1968
[21] Appl. No.: 779,987

[30] Foreign Application Priority Data
Dec. 2, 1967 Netherlands.......................6716437

[52] U.S. Cl...... 260/479 R; 260/613 R; 260/619 A; 424/299; 424/340; 424/341; 424/346
[51] Int. Cl.² .................. C07C 39/16; C07C 39/17; C07C 43/20; C07C 69/02
[58] Field of Search......... 260/479 R, 619 A, 613 R Primary Examiner—Norman Morgenstern
Attorney, Agent, or Firm—Frank R. Trifari; Norman N. Spain

[57] ABSTRACT

Substituted diphenyl adamantylidene methanes. Examples of substituents on the para positions of the phenyl groups are propoxy and acetyloxy. The compounds have estrogenic activities.

7 Claims, 7 Drawing Figures

U.S. Patent  February 3, 1976  3,936,491
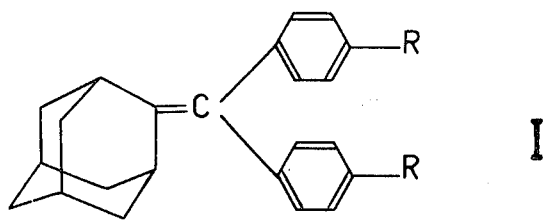 I
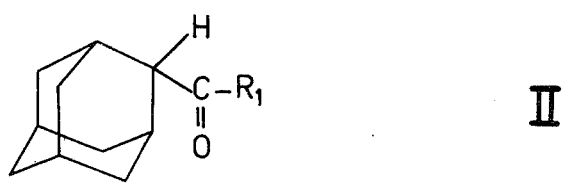 II
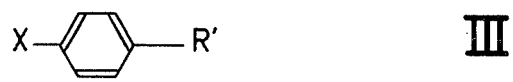 III
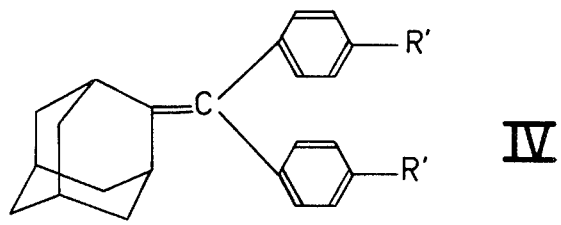 IV
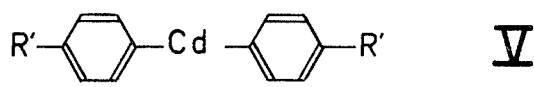 V
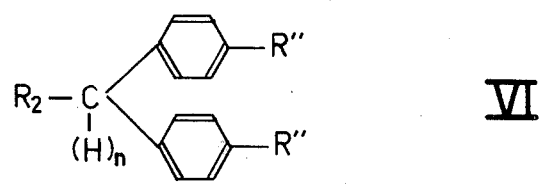 VI
 VII
INVENTOR.
VOLKERT CLAASSEN
BY
AGENT

ADAMANTYLENE COMPOUNDS

This invention relates to new adamantylene compounds of formula I

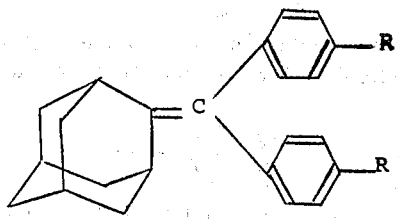

in which formula R is a hydroxy group, an alkoxy group having 1 to 3 carbon atoms or an acyloxy group having up to 20 carbon atoms.

As examples of the groups which are denoted by R may be mentioned: methoxy, ethoxy, propoxy, isopropoxy, formyloxy, acetyloxy, propionyloxy, caproyloxy, palmityloxy, stearyloxy, succinyloxy, tartaryloxy, benzoyloxy, fumaryloxy, and the like. In the case R is an acid radical of a multivalent acid having a free carboxyl group, said carboxyl group may be present in the salt form, for example, as Na, K, Ca or ammonium salt.

It is known that some adamantane derivatives substituted in 1 or 2 positions, have antiviral activities. It has surprisingly been found that the novel adamantylene compounds of the invention exhibit in mammals, estrogenic and antifertile activities and in addition show antiprogestational activities.

Particularly active compounds are di(p.methoxyphenyl)-adamantylidene methane, di(p.hydroxyphenyl)-adamantylidene methane and di(p.acetyloxyphenyl-adamantylidene methane. Of these compounds, di(p.acetyloxyphenyl)-adamantylidine methane shows a strong antiprogestational activity and di(p.hydroxyphenyl)-adamantylidine methane shows a very strong antiprogestational activity.

On the basis of these properties, the compounds of formula I may be used as antifertility agents. They may alternatively be used to induce menstruation. The daily dose is about 7-21 mg/kg.

Generally the compounds will be administered in humans orally at a dosage of about 500 to 1500 mg/day, 1200 mg/day being preferred. To prevent fertility this dosage is administered during 5-7 days at the end of the menstrual cycle when gravidity is probable or from day 20 to day 25 of the cycle to prevent nidation. To induce menstruation this dosage is administered from day 24 to day 27 of the cycle.

The estrogenic properties of the compounds is shown in the following experiments.

a. Three-week-old, infantile female rats were injected subcutaneously with a compound according to the invention. Up to the end of the experiments 2 mg per 48 hours were thus administered. The estrogenic activity of a substance is expressed in this test in a premature opening of the vagina. Both the treated group and the blank group consisted of 8 rats.

b. Eight three-week-old infantile castrated female rats were injected subcutaneously one daily with 4 to 5 γ of the compound to be tested. The estrogenic activity of the substance to be tested is expressed in this test also in the opening of the vagina in the treated group. In addition the uterus of the experimental animals was weighed after dissection. The estrogenic activity is expressed in a higher weight of the uterus of the treated animals than of the animals of the blank group.

c. Six female rats were castrated. Two weeks later the vagina epithelium had given rise to a castration picture. At that instant 1 mg of a compound to be tested was administered subcutaneously daily to the animals. Vaginal smears were daily' investigated microscopically. In this test a peripheric estrogenic activity is expressed in the disappearance of leucocytes and the renewed formation of epithelium and horn cells.

d. Groups of twenty castrated adult female rats were injected subcutaneously two weeks after castration with a compound to be tested. One day later the same quantity was administered twice. After 24, 40, 48 and 64 hours vaginal smears were made and investigated microscopically. The injected dose of substance varied for each individual group and lay between 2 and 4000 γ per time.

e. In the so-called Rubin test, 8 infantile female mice of three weeks old were injected subcutaneously for three days with a compound to be tested. After dissection the weight of the uteri was compared with that of the animals of the blank group. The dose varied from 4 γ to 1 mg daily.

The antiprogestatinaal activity of the compounds according to the invention was established in the so-called anti-Clauberg test. In this test groups of 4 infantile female rabbits were daily injected for 8 days with 4 units of estradiol monobenzoate. This substance was then administered daily in a quantity of 0.8 units, together with 150 γ of progesterone subcutaneously and 2 to 2000 γ of the compound to be tested also subcutaneously. In this test, the antiprogestational activity of the compound to be tested is expressed in the inhibition of the secretory changes of the endometrium caused by the injected progesterone.

The anti-fertile properties of the compounds were found in a test in which 1 male rat was placed with 3 adult female rats. The next day vaginal smears were made and tested for the presence of sperm. The female rats in which sperm was found were subcutaneously administered from the first day of pregnancy with 20 to 2000 γ of the compound to be tested for 6 days. On the 15th day of pregnancy dissection was carried out and the number of living young ones, dead young ones and foetus residues in the uterus were determined. The antifertile activity in this test is expressed in a reduction of the number of living young ones with respect to the blank group.

The results of these tests are given below for the compounds Du 34,394 (compound of formula I wherein R = OCH$_3$), Du 34,427 (compound of formula I wherein R = OH) and Du 34,444, compound of formula I wherein

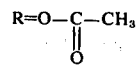

ESTROGENIC TESTS

Test a

With DU 34,394 — The vagina in each of the eight rats treated with the drug opened between day 3 and day 7. In the blanks in 7 out of 8 rats the vagina only opened between day 8 and day 14.

Test b

1. With Du 34,427—In each of the eight rats treated with the compound Du 34,427 at a dose of 4 g/day the vagina opened on day 4 or 5. In the blanks (8 rats) the vagina did not open at all. The uterus weight of the treated rats averaged 60 mg. that of the untreated rats averaged 27 mg.

Test b

2. With Du 34,444—In each of the eight rats treated with the compound Du 34,444 at a dose of 5g/day the vagina opened at day four or five. In the blanks the vagina did not open at all. The average weight of the uterus of the treated rats was 57 mg. that of the untreated rats was 27 mg.

Test c (Dose of 1 mg/day employed)

1. With Du 34,394—With the administration of Du 34,394 the vaginal smears exhibited horn cells. The average weight of the uterus of the treated rat was 139 mg, that of the untreated rat, 61 mg.
2. With Du 34,427—With the administration of Du 34,427, the vaginal smears exhibited horn cells. The average uterus weight of the treated rats was 205 mg, that of the untreated rats, 61 mg.
3. With Du 34,444—With the administration of Du 34,444, the vaginal smears exhibited horn cells. The average uterus weight of the treated rats was 187 mg, that of the untreated rats 61 mg.

In all cases, the vaginal smears of the untreated rats exhibited leucocytes epithelium cells plus horn cells.

Test d

Ten rats were treated with 0.25 mg of the test compounds and there were ten blanks. The compounds tested were Du 34,427 and Du 34,444. Both compounds exhibited the following results: After 24 hours the vaginal smears showed epithelium cells, after 40 hours, 48 hours and 64 hours the vaginal smears showed horn cells.

The blanks showed the same results as in test c.

Test e

With the administration of 2 mg of Du 34,394 the average uterus weight was 37.0 mg, that of the blanks was 18.9 mg.

With the administration of 0.25 mg of Du 34,427 the average uterus weight was 33.7 mg and that of the blanks was 14.0 mg.

Antiprogestational Activity

Du 34,394 administered in 3 mg dose produced no effect.

Du 34,427 administered in 0.2 mg dose produced complete effect.

Du 34,444 administered in 0.8 mg dose produced complete effect.

Antifertility Activity

Du 34,394 — $ED_{50}$ = 1 mg
Du 34,427 — $ED_{50}$ = 0.025 mg
Du 34,444 — $ED_{50}$ = 0.038 mg

The invention also relates to novel methods for preparing the new adamantylidene compounds.

The compounds of the invention may be prepared by starting from a compound of formula II

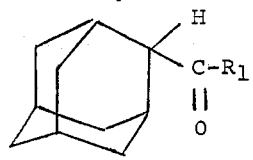

in which formula $R_1$ is an alkoxy group, an aralkoxy group, a halogen atom, preferably a chlorine atom, or a group

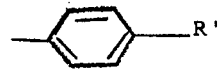

in which formula R' is an alkoxy group, a benzyloxy group or a pyranyloxy group. These compounds may be reacted, for example, in diethyl ether, tetrahydrofurane, dioxane and similar solvents with a compound of formula III

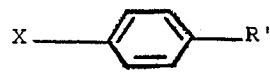

in which compounds of formula IV are formed after hydrolysis of the reaction product. In formula III, X means a lithium atom or the group HalMg—, in which Hal is a halogen atom. When R' in the starting substances is a benzyloxy group, for example, a t. butyloxy- group, a free hydroxyl group may be obtained therefrom in the reaction product by hydrolysis. Particularly the benzyloxy group may be split off also by hydrogenolysis, for example, with Pt or Pd/C and hydrogen. The resulting hydroxy groups may be converted into acyloxy groups with an acid, acid halide or acid anhydride derived from an acid having up to 20 carbon atoms.

The starting substances of formula II, in which formula $R_1$ is a halogen atom, an alkoxy group or an aralkoxy group, may be obtained in the conventional manner from 2-adamantyl carboxylic acid, which substance may be prepared by reacting 2-hydroxy adamantane with formic acid and sulphuric acid. The ketones of formula II are obtained, for example, by reacting 2-adamantyl carboxylic acid chloride with a cadmium reagent of formula V

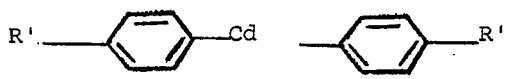

which may be obtained by reacting cadmium chloride with a compound of formula III.

The compounds according to the invention may alternatively be prepared by reacting adamantanone with a compound of formula VI

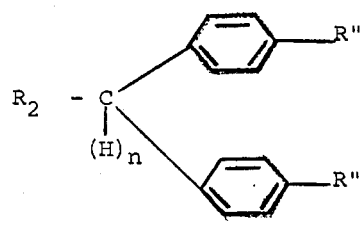

in which formula $R_2$ is the group $= P(C_6H_5)_3$ in which case $n = 0$, or the group $- P = O(OCH_3)_2$ or $P = O(OL_2H_5)_2$ in which cases n = 1 or the group $= P(A)_3$ wherein A is lower alkyl such as n. butyl, n. propyl, ethyl and methyl and also p-anisolyl and p. tolyl. R'' in this formula is a hydroxy group, an alkoxy group, an acyloxy group having up to 20 carbon atoms, or a benzyloxy group or a pyranyloxy group. The reaction may be carried out, for example, in inert solvent, for example, methanol, petroleum ether, dimethyl sulfoxide, and the like. In case a phosphorane is reacted, reactions are preferably carried out in a medium made alkaline, for example, with sodium alcoholate, phenyl lithium, NaOH and the like. After the coupling reaction benzyloxy groups, pyranyloxy groups and alkoxy groups, for example, t. butyloxy groups, may be converted into free hydroxy groups by hydrolysis. The benzyloxy group may alternatively be split off easily by catalytic hydrogenation.

The compounds of formula I may be prepared alternatively by reacting 2-adamantyl carboxylic acid chloride, under the influence of a Friedel-Crafts catalyst with a compound of formula VII,

in which formula R''' is a hydroxy group, an alkyloxy group, a pyranyloxy group or a benzyloxy group, and splitting off from the reaction product pyranyloxy groups benzyloxy groups or alkoxy groups having more than 3 carbon atoms, by hydrolysis or hydrogenolysis. Compounds in which R is an acyloxy group may be obtained by acylating subsequently the hydroxy compound with an acid, acid halide or acid anhydride. The coupling reaction may be carried out in the reagent of formula VII as a solvent or in an invet solvent, for example, carbon disulphide and the like.

The compounds according to the invention can be compounded into suitable forms for administration, for example, tablets, coated tablets, capsules, pills, powders, injection liquids and the like by means of the conventional methods and by the use of pharmaceutically acceptable carriers and auxiliary substances.

As carriers, there may be used, for example, water, glycerine, chalk, calcium phosphate, lactose and powdered sugar (saccharose), or mixtures of these substances. The use of sugars as a carrier has the advantage that these substances have a pleasant taste.

Uncoated tablets and coated tablets may contain in addition swelling agents which cause the preparation to easily disintegrate in water. As such may be used, for example, potato starch, maize starch, arrow root (amylum marantae), carboxymethyl cellulose. In addition lubricants may be used, for example, talcum, magnesium stearate and calcium stearate.

As preservatives may be added such compounds as for example, methyl-p.hydroxy benzoate, propyl-p.hydroxybenzoate and benzyl alcohol.

As surface-active substances there may be used, for example, mono-, di-, or tri-esters of, for example, lauric acid, palmitic acid, stearic acid, ricinic acid, and oleic acid with a poly alcohol, for example, sorbitan, mannitan, mannide and glycerol and in addition polyoxyethylene derivatives of inter alia the above-mentioned esters.

Tablets may have, for example, the following composition:
100 mg di-p.hydroxyphenyl adamantylidene methane.
25 mg glycerly monostearate
250 mg powdered lactose.
50 mg polyvinyl pyrrolidone.
2 mg magnesium stearate.
10 mg talcum.

The invention will now be described in greater detail with reference to the following examples:

Tablets were prepared as follows:
100 g of di-p-hydroxyphenyl adamantylidene methane and 25 g of glyceryl monostearate were dissolved in 250 ml of methylene chloride. The solution was added to 250 g of powdered lactose, after which the mixture was left to stand until the methylene chloride was evaporated. The residue was sieved through a 80 mesh sieve and then mixed with 50 g of polyvinyl pyrrolidone. After wetting with a mixture of ethanol and water 1 : 1, the mixture was granulated and dried. 2 g of magnesium stearate and 10 g of talcum were added to the granulate which was then compressed to 1000 437-mg tablets.

Capsules may have the following composition:
100 mg of di-p.acetoxyphenyl adamantylidene methane
20 mg sodium lauryl sulfate
2 mg magnesium stearate.
50 mg powdered lactose.

Capsules were prepared as follows:
100 g of di-p.acetoxyphenyl adamantylidene methane were mixed with 20 g of sodium lauryl sulphate and then ground. The mixture was mixed with 2 g of magnesium stearate and 50 g of powdered lactose and then dispensed in capsules.

Capsules having a composition of
100 mg di-p.methoxyphenyl-adamantylidene methane and
0.3 ml polyoxyethylene glycol
were obtained by grinding 100 g of di-p.methoxy phenyl adamantylidene methane in a ball mill in the presence of 100 ml of polyoxylthylene glycol, until the average diameter was 2 μ. 200 ml of polyoxyethylene glycol were then added to the ground substances, after which the whole was mixed and then dispensed in soft gelatin capsules.

EXAMPLE 1 a. 2-Adamantylcarboxylic acid 4.5 g of 2.hydroxyadamantane were dissolved in 30 mls of HCOOH 98–100 %, and this solution was added dropwise, while stirring vigorously, to 1.5 l. of $H_2SO_4$ 96% cooled to 5°C. Stirring was then continued at the same temperature for 90 minutes and the mixture was finally poured out on ice. NaOH was added to the mixture until it has a pH of approximately 1 and the formed precipitate was extracted with diethyl ether. The extract was dried over $Na_2SO_4$ and the solvent was then evaporated. The cruse 2-adamantyl carboxylic acid was thus obtained, which was purified by two crystallizations from 70% ethanol. The purified acid had a melting point of 142–144°C.

b. 2-Adamantyl carboxylic ethyl ester 7 g of 2-adamantyl carboxylic acid were refluxed for 30 minutes with 15 ml of $SOCl_2$. HCl escaped. The excess of $SOCl_2$ was then evaporated and the crude acid chloride dissolved twice in benzene, the benzene being evaporated each time. 1.8 g of absolute alcohol were then added dropwise carefully in 25 ml of absolute diethyl e ether. In this manner a solution of 2-adamantyl carboxylic ethyl ester was obtained.

c. Adamantylidene di-(p-methoxyphenyl)methane

The solution of 2-adamantyl carboxylic ethyl ester described in 1b was added dropwise to a solution prepared according to Grignard from 15.6 g of anisol and 2.25 g of magnesium in 50 ml of diethyl ether. Some heat evolved. The solution was then refluxed for one hour and then cooled and poured out on 75 mls of a saturated solution of NH$_4$Cl cooled to 0°C. The organic layer was separated, washed once with a saturated solution of NH$_4$Cl, twice with water and dried on Na$_2$SO$_4$. The solvent and an excess of 2-bromo anisol were then evaporated. The remaining semisolid mass was dissolved in benzene and chromatographed over silica gel. Thus crystalline 2-adamantylidene di-(p.methoxy phenyl)methane was obtained which after recrystallization from absolute alcohol had a melting point of 151.5°–153°C.

EXAMPLE 2

2-Adamantylidene di-(p.hydroxyphenyl)methane 1.9 g of 2-adamantylidene-di(p.methoxyphenyl)methane were dissolved in 5.5 ml of diethylene glycol (boiling point 220°C) and 1.3 gms of KOH were added to this solution after which water was distilled off until the temperature of the mixture was 210°–220°C. The solution was then refluxed for 3½ hours and then poured on ice. The water layer was extracted with ether and then acidified with 5 nHCl, a solid precipitating. This solid was then taken up with ether. After drying on Na$_2$SO$_4$, the solvent was evaporated and the crude remaining 2-adamantylidene di(p.hydroxyphenyl)methane was recrystallized from petroleum ether (boiling point 60°–80°C) and very little absolute alcohol. The resulting product consisted of cream-colored laminae m.p. 258°–259°C.

EXAMPLE 3

2.Adamantylidene-di-(p.acetoxyphenyl) methane 1 g of 2-adamantylidene di-(p.acetoxyphenyl) methane was dissolved in 10 ml of acetic anhydride after which one drop of H$_2$SO$_4$ 96% was added. Some heat evolved. The solution was then heated on a steam bath for 30 minutes after which the mixture was cooled and poured in water; this mixture was finally heated on a steam bath for 30 minutes while stirring vigorously. After cooling it was extracted with ether, the ethereal solution was washed twice with a saturated solution of NaHCO$_3$ and once with water, dried on Na$_2$SO$_4$ and evaporated in vacuo at room temperature. The evaporated residue was crystallized from alcohol. In this manner a product was obtained which consisted of cream-colored laminae, melting point 160.5° – 161.5°C.

EXAMPLE 4

2-Adamantylidene di-(p.methoxyphenyl)-methane 2.0 g of di-(p.methoxyphenyl)methylchloride, which was prepared as described in J. Chem. Soc. 1958, 1925, were mixed with 1.5 g of trimethylphosphite and the mixture was heated for 1 hours, during which the temperature was gradually raised from 140°C to 200°C. During the first 30 minutes gas bubbles were observed of escaping methyl chloride. The crude di-(p-methoxypjenyl)methyl dimethyl phosphonate was thus obtained as a yellow oil. It was dissolved in 10 mls of absolute dimethoxy ethane. A suspension of 0.32 g of NaH. in dry dimethoxy ethane was added and the whole was stirred at room temperature for 60 minutes. Gas evolved. 1.14 g of adamantanone in 10 mls of dimethoxy ethane were then added dropwise. The mixture was then kept at room temperature for 30 minutes while stirring and then refluxed for 4 hours. 100 ml of water were added and the water layer was then extracted three times with diethyl ether. The ether extract was dried over Na$_2$SO$_4$ after which the ether was evaporated. The remaining crude 2-adamantylidene di(p.methoxyphenyl) methane was finally crystallized from methanol and thus obtained as a pure product.

EXAMPLE 5 a. 2.Adamantyl-p-methoxyphenylketone

A solution according to Grignard was prepared in the conventional manner from 2.3 g of magnesium and 18.7 g of bromoanisol in 55 mls of absolute diethyl ether. 18.3 g of CdCl$_2$ which had been dried overnight at 12½°C were then added to this solution while stirring vigorously. The solution was then refluxed for 90 minutes. The ether was evaporated. 20 mls of absolute benzene were then added and finally it was distilled off in vacuo. 70 ml of absolute benzene were then added and 19.8 g of 2-adamantyl carbonyl chloride (prepared according to 1b) in 70 mls of absolute benzene were added dropwise in approximately 10 minutes while stirring vigorously. The solution was then refluxed for 2½ hours while stirring vigorously, after which the mixture was stirred overnight at room temperature. 100 g of ice and 1.9 ml of H$_2$SO$_4$ 96% were finally added. The organic layer was separated and the water layer extracted once with benzene. The collected benzene solutions were washed once with water, twice with a saturated NaHCO$_3$ solution and then twice with water. The solution was dried over C$_a$Cl$_2$ and the benzene was then evaporated. The remaining oil was distilled off in vacuo and in this manner 2-adamantyl-p-methoxyphenylketone was obtained as a pure product, all manipulations prior to mixing the reaction product with ice being carried out in a nitrogen atmosphere.

b. 2-adamantylidene di(p.methoxyphenyl)methane

To a solution according to Grignard prepared from 2.3 g of magnesium and 18.7 g of bromoanisol in 55 ml of absolute ether, a solution of 27 g of 2-adamantyl-p.methoxy-phenylketone in 70 ml of absolute ether was added dropwise. The solution started boiling. After everything had been added, the solution was refluxed for 1 hour. The mixture was then poured on a saturated solution of NH$_4$Cl cooled to 0°C. The organic layer was separated, washed once with a saturated solution of NH$_4$Cl and twice with water. Then it was dried over Na$_2$SO$_4$ and the solvent was evaporated. The resulting crude 2-adamantylidene di(p.methoxy-phenyl) methane was purified as described in 1c.

EXAMPLE 6 a. Adamantylidene di-(p.benzyloxyphenyl) methane

A grignard solution was prepared in 50 ml of ether from 10.5 g of 1-bromophenyl benzyl ether and 1 g of Mg. 4.2 g of 2-adamantylcarboxylic ethyl ester prepared as described in 1b, were added to the solution and according to the method in 1c adamantylidene di(p.benzyloxyphenyl) methane was obtained.

b. Adamantylidene di-(p.hydroxyphenyl) methane

The crude adamantylidene di-(p.benzyloxyphenyl)methane mentioned in 6a was dissolved in 100 ml of ethyl acetate. 300 mgs of Pd/C (10% were added; hydrogenation was carried out in the conventional manner. After 820 ml of H$_2$ had been taken up, the catalyst was filtered off and the solvent evaporated. The crude adamantylidene di-(p.hydroxyphenyl) methane was purified as described in example 2.

While we have described our invention in connection with specific embodiments and applications, other modifications thereof will be readily apparent to those skilled in this art without departing from the spirit and scope of the invention as defined in the appended claims.

What I claim is:

1. An adamantylidene compound of the formula

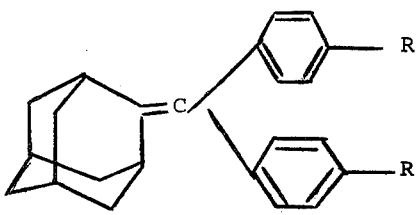

wherein R is a member selected from the group consisting of hydroxy, alkoxy of 1 to 3 carbon atoms inclusive, alkanoyloxy of up to 20 carbon atoms and benzoyloxy.

2. A compound which is represented by the formula:

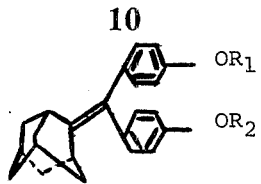

wherein $R_1$ and $R_2$ are identically hydrogen or alkyl of 1 through 3 carbon atoms.

3. A compound of claim 1 wherein R is methoxy and the compound is di-(p.methoxyphenyl) adamantylidene-methane.

4. The compound of claim 1 wherein R is hydroxy and the compound is di-(p.hydroxyphenyl) adamantylidene-methane.

5. A compound of claim 1 wherein R is acetyloxy and the compound is di(p.acetyloxyphenyl) adamantylidene-methane.

6. 2[bis(p-hydroxyphenyl) methylene] adamantane.

7. 2[bis(p-methoxyphenyl) methylene] adamantane.

* * * * *